(12) United States Patent
Nishida et al.

(10) Patent No.: US 8,945,080 B2
(45) Date of Patent: Feb. 3, 2015

(54) DISPOSABLE DIAPER

(75) Inventors: Motoko Nishida, Mima-gun (JP); Yuki Hasebe, Mima-gun (JP)

(73) Assignee: Livedo Corporation, Ehime (JP)

( * ) Notice: Subject to any disclaimer, the term of this patent is extended or adjusted under 35 U.S.C. 154(b) by 280 days.

(21) Appl. No.: 13/521,845

(22) PCT Filed: Jan. 13, 2011

(86) PCT No.: PCT/JP2011/000147
§ 371 (c)(1),
(2), (4) Date: Jul. 12, 2012

(87) PCT Pub. No.: WO2011/089871
PCT Pub. Date: Jul. 28, 2011

(65) Prior Publication Data
US 2012/0289924 A1 Nov. 15, 2012

(30) Foreign Application Priority Data

Jan. 25, 2010 (JP) .................................. P2010-13136

(51) Int. Cl.
*A61F 13/15* (2006.01)

(52) U.S. Cl.
USPC ........... 604/389; 604/387; 604/391; 604/394; 604/396

(58) Field of Classification Search
USPC .......................... 604/389, 387, 391, 394, 396
See application file for complete search history.

(56) References Cited

U.S. PATENT DOCUMENTS

| 5,897,546 | A | 4/1999 | Kido et al. |
| 6,063,466 | A | 5/2000 | Tuschy et al. |
| 2003/0100878 | A1 | 5/2003 | Leak et al. |
| 2004/0236303 | A1 | 11/2004 | Igaue et al. |
| 2007/0129700 | A1 | 6/2007 | Yoshida |

FOREIGN PATENT DOCUMENTS

| CN | 1136427 A | 11/1996 |
| CN | 1177285 A | 3/1998 |
| EP | 0756855 A1 | 2/1997 |
| EP | 0756855 B1 | 2/1997 |
| EP | 1688116 A1 | 8/2006 |

(Continued)

OTHER PUBLICATIONS

Office Action from Taiwan Patent App. No. 100101731 (Mar. 6, 2014).

(Continued)

*Primary Examiner* — Jacqueline F. Stephens
(74) *Attorney, Agent, or Firm* — Cermak Nakajima & McGowan LLP; Tomoko Nakajima

(57) ABSTRACT

Each of first fastening tapes and second fastening tapes provided on both left and right sides of a disposable diaper has a first fastening part and a second fastening part which are away from each other. When putting the disposable diaper on a slender wearer, the second fastening tape is fastened on an attachment part of main body part so as to be laid over the first fastening tape. In the second fastening tape, since an intermediate area is provided between the first fastening part and the second fastening part, a total area of fastening parts can be reduced. Since a distance between an outer edge of the first fastening part and an inner edge of the second fastening part is made larger than a width of a tape base at the intermediate area in the first fastening tape, the second fastening tape can be easily fastened.

16 Claims, 5 Drawing Sheets

(56) References Cited

FOREIGN PATENT DOCUMENTS

| JP | 10-028703 A | 2/1998 |
| JP | 2004-344514 A | 12/2004 |
| JP | 2005-160506 A | 6/2005 |
| JP | 2007-143633 A | 6/2007 |
| JP | 2008-067831 A | 3/2008 |
| JP | 2009-061157 A | 3/2009 |
| WO | WO2005/051276 A1 | 6/2005 |
| WO | WO2009/123253 A1 | 10/2009 |

OTHER PUBLICATIONS

Office Action from Japanese Patent App. No. 2010-13136 (Jul. 11, 2013).
Office Action from Chinese Patent App. No. 2011800057833 (Jan. 6, 2014) with English language translation thereof.
International Search Report and Written Opinion for PCT Patent App. No. PCT/JP2011/000147 (May 26, 2011).
Notice of Allowance for Korean Patent App. No. 10-2012-7015844 (Aug. 12, 2013).

II—II

DISPOSABLE DIAPER

This application is a national phase entry under 35 U.S.C. §371 of PCT Patent Application No. PCT/JP2011/000147, filed on Jan. 13, 2011, which claims priority under 35 U.S.C. §119 to Japanese Patent Application No. 2010-013136, filed Jan. 25, 2010, both of which are incorporated by reference.

TECHNICAL FIELD

The present invention relates to a disposable diaper.

BACKGROUND ART

An open-type (tape-type) disposable diaper where a portion located on the front side of a wearer and a portion located on the back side are fastened around the waistline of the wearer by fastening tapes to wear the disposable diaper is conventionally used as one of disposable diapers for receiving excrement from a wearer. For example, in Japanese Patent Application Laid-Open No. 10-28703 (Document 1), disclosed is a disposable diaper where a pair of fastening tapes attached on a back sheet at left and right side portions of a back side part is fastened to a landing tape provided on the back sheet at a front side part. A plurality of convex members in a mechanical fastener are arranged in a left-right direction on a tape main body of each fastening tape, and these convex members are releasably fastened to the landing tape which is a concave member in the mechanical fastener.

In a disposable diaper disclosed in Japanese Patent Application Laid-Open No. 2004-344514 (Document 2), hook members are provided on a pair of rear wings which is provided at left and right sides of back waist region, and the hook members are releasably fastened to a loop member which is provided on an outer surface of front waist region. In the disposable diaper, the hook members consist of a plurality of hook assemblies which are separated from one another.

In Japanese Patent Application Laid-Open No. 2008-67831 (Document 3), disclosed is a disposable absorbent product where two tape-like fasteners are located at each of left and right side portions of back waist part in an absorbent product main body so as to be apart from each other in an up-down direction. One hook member to engage with a loop member of a loop fastener provided on an outer surface of front waist part is provided on an inner surface of each tape-like fastener, and a loop member which is capable of engaging with the hook member is provided on an outer surface of the tape-like fastener.

In Document 3, it is proposed that, in each of the left and right side portions, the hook member of upper tape-like fastener is engaged with the loop member of the loop fastener on the front waist part, the hook member of lower tape-like fastener is engaged with the loop member provided on the outer surface of the upper tape-like fastener, and therefore the absorbent product is put on the wearer so as to suit the wearer's figure. It is also proposed that the hook members of the tape-like fasteners provided on one side portion of the left and right side portions are engaged with the loop member of the loop fastener, the hook members of the tape-like fasteners provided on the other side portion are engaged with the loop members provided on the outer surfaces of the tape-like fasteners on the one side portion, and therefore the absorbent product is put on the wearer so as to suit the wearer's figure.

In the disposable diaper of Document 1, it is not considered how to fasten the fastening tapes on the front side part when putting the disposable diaper on a slender wearer or the like (the same applies to Document 2). In Document 3, it is proposed to fasten one tape-like fastener on another tape-like fastener in accordance with the wearer's figure. However manufacture of the absorbent product is complicated and an amount of hook members used for the absorbent product is increased, because there is a need to provide the loop member on the outer surface of each tape-like fastener and to provide the hook member, to engage with the loop member, on the inner surface.

SUMMARY OF INVENTION

The present invention is intended for a disposable diaper. It is an object of the present invention to easily fasten a fastening tape, which is to be laid on the other fastening tape in fastening the fastening tapes, on a front part while a total area of fastening parts is reduced.

The disposable diaper according to the present invention comprises: a sheet-like main body part having a front part, a crotch part and a back part which are arranged in this order along a longitudinal direction; and a pair of connection parts attached to both side portions of the back part, the pair of connection parts being to be fastened to an outer surface of the front part to connect the both side portions with both side portions of the front part; wherein each of the pair of connection parts comprises two fastening tapes each extending in a left-right direction, the two fastening tapes being arranged in the longitudinal direction, and each of the two fastening tapes comprises: a band-like tape base; a first fastening part provided on an inner surface of the tape base so as to lie across the tape base in the longitudinal direction, the first fastening part being capable of fastening itself to the outer surface of the front part; and a second fastening part provided on the inner surface of the tape base so as to lie across the tape base in the longitudinal direction, the second fastening part being away from the first fastening part toward the main body part and being capable of fastening itself to the outer surface of the front part; and a distance between an edge of the first fastening part which is closer to a tip of the tape base than the other edges and an edge of the second fastening part which is closer to the main body part than the other edges in one fastening tape, is larger than a width of the tape base at a position between the first fastening part and the second fastening part in the other fastening tape.

In the present invention, it is possible to easily fasten the fastening tape, which is to be laid on the other fastening tape in fastening the fastening tapes, on the front part while a total area of fastening parts is reduced.

According to a preferred embodiment of the present invention, a length, in the left-right direction, of an area between the first fastening part and the second fastening part in the one fastening tape is equal to or larger than 25% of the width of the tape base at the position in the other fastening tape. It is therefore possible to prevent, to some extent, a (portion of) fastening part from being provided on a portion which is more likely not to be used for fastening the one fastening tape when the one fastening tape is laid on the other fastening tape to be fastened on the front part.

More preferably, the length, in the left-right direction, of the area between the first fastening part and the second fastening part in the one fastening tape is equal to or larger than the width of the tape base at the position in the other fastening tape. Therefore, when the fastening tapes are fastened with the one fastening tape lying on the other fastening tape, at least one portion of each of the first fastening part and the second fastening part in the one fastening tape can be fastened on the front part more easily.

According to another preferred embodiment of the present invention, a width of each fastening tape gradually decreases toward a tip of the tape base. Therefore, when the fastening tapes are fastened, the first fastening part of one fastening tape which is fastened later than the other fastening tape can be easily fastened on the front part with avoiding the other fastening tape.

According to an aspect of the present invention, two tape bases of the two fastening tapes are portions of one sheet in each of the pair of connection parts, and the two tape bases are continuous with each other through a connection portion of the one sheet located near the main body part, and second fastening parts of the two fastening tapes lie at an outside, with respect to the left-right direction, of the connection portion in the one sheet. It is therefore possible to prevent stiffness of root portions of the two fastening tapes from being excessively large and to easily deform the two fastening tapes at the root portions.

According to another aspect of the present invention, since positions of the first fastening part and the second fastening part are recognizable at an outer surface side of the tape base in each of the two fastening tapes, the first fastening part and the second fastening part of one fastening tape which is fastened on the front part later than the other fastening tape can be prevented from overlapping extensively with the other fastening tape.

These and other objects, features, aspects and advantages of the present invention will become more apparent from the following detailed description of the present invention when taken in conjunction with the accompanying drawings.

DESCRIPTION OF EMBODIMENTS

Figure 1:
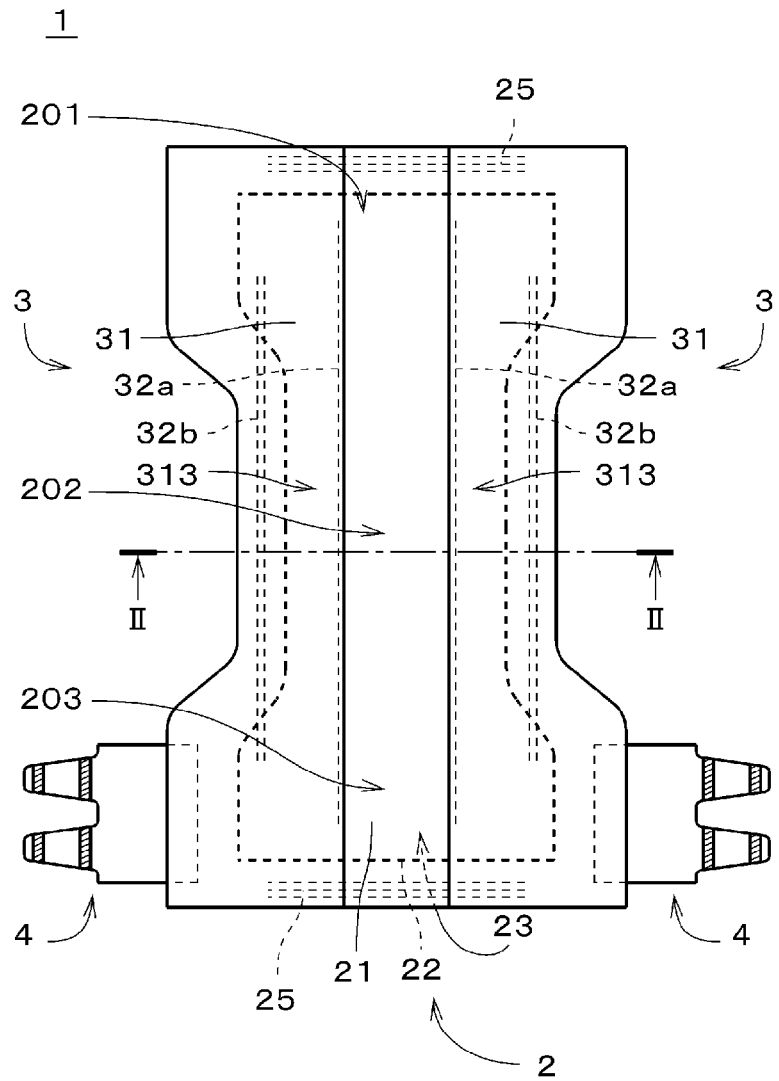
FIG. 1 is a plan view of a disposable diaper in accordance with a preferred embodiment.

FIG. 1 is a plan view of a disposable diaper 1 in accordance with a preferred embodiment of the present invention, and FIG. 1 shows a state where the disposable diaper 1 is developed. The disposable diaper 1 is an open-type (tape-type) disposable diaper where a portion located on the front side of a wearer and a portion located on the back side are fastened around the waistline of the wearer by both left and right connection parts 4 when it is worn, and the disposable diaper 1 receives excrement from the wearer. FIG. 1 shows a surface of the disposable diaper 1, which comes into contact with the wearer when the disposable diaper 1 is worn (i.e., the surface is to face the wearer).

Figure 2:
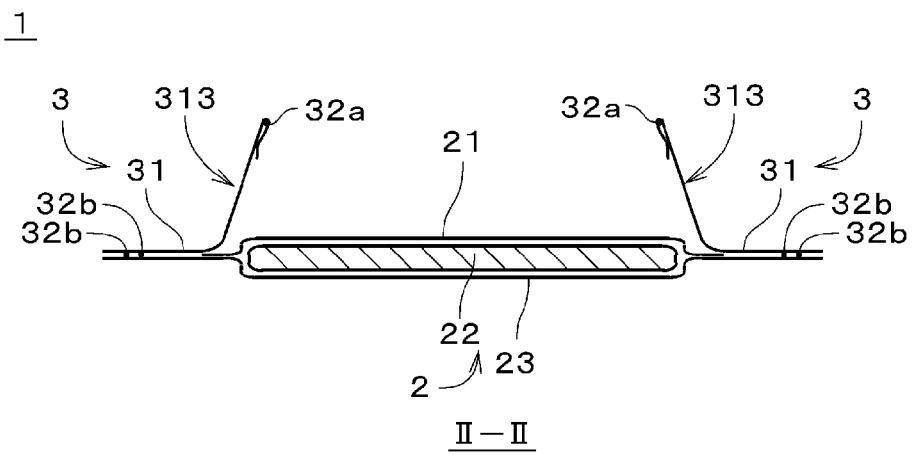
FIG. 2 is a cross-sectional view of the disposable diaper.

FIG. 2 is a cross-sectional view of the disposable diaper 1 taken along a line II-II in FIG. 1 where the disposable diaper 1 is cross-sectioned with a plane orthogonal to its longitudinal direction (i.e., an up-down direction in FIG. 1). As shown in FIGS. 1 and 2, the disposable diaper 1 has an almost sheet-like main body part 2 and a pair of side sheets 3 which is located on both side portions of the main body part 2 (i.e., the side portions are positioned at both sides of the main body part 2 in a left-right direction orthogonal to the longitudinal direction) and which extends across almost the entire length of the main body part 2 in the longitudinal direction.

An upper portion 201 of the main body part 2 in FIG. 1 is to be positioned on (skin of) the front side (stomach side) of the wearer, and a lower portion 203 in FIG. 1 is to be positioned on the back side of the wearer. In the following description, the upper portion 201 and the lower portion 203 are referred to as a "front part 201" and a "back part 203", respectively, and a portion 202 to face a crotch region of the wearer at a position between the front part 201 and the back part 203 is referred to as a "crotch part 202". The crotch part 202 is continuous with the front part 201 and the back part 203. In the disposable diaper 1, the main body part 2 has the front part 201, the crotch part 202 and the back part 203 which are arranged in this order along the longitudinal direction, and widths of the front part 201 and the back part 203 are larger than a width of the crotch part 202.

Figure 3:
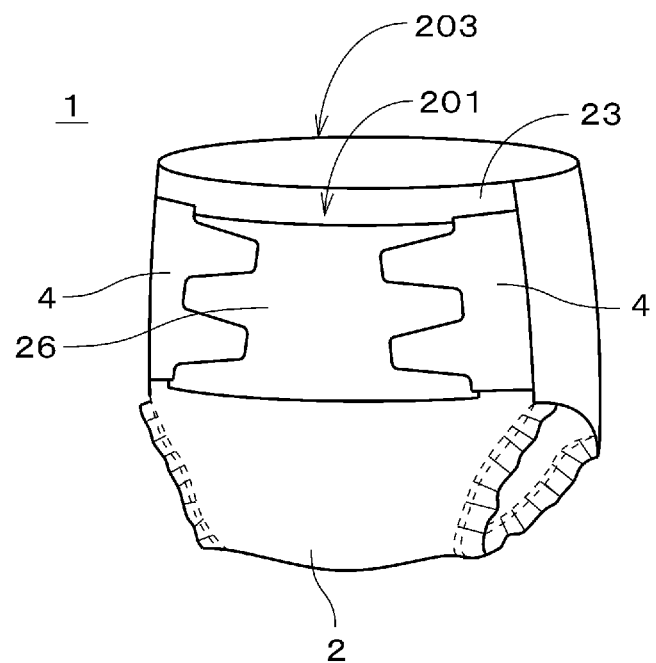
FIG. 3 is a perspective view of the disposable diaper.

The disposable diaper 1 further has a pair of connection parts 4 attached to both side portions of the back part 203. When putting the disposable diaper 1 on the wearer, as shown in FIG. 3, the pair of connection parts 4 is fastened (attached) on an attachment part 26 (a part to be fastened by the pair of connection parts 4) provided on an outer surface of the front part 201 (i.e., the outer surface is different from a surface contacting with the wearer) in the state where the front part 201 and the back part 203 of the main body part 2 are made to contact with the front side and the back side of the wearer, respectively. Therefore, the both side portions of back part 203 are connected with both side portions of the front part 201.

As shown in FIGS. 1 and 2, the main body part 2 has a liquid-pervious top sheet 21, a water-repellent or liquid-impervious back sheet 23, and an absorbent core 22 located between the top sheet 21 and the back sheet 23. In FIG. 2, respective constituents of the disposable diaper 1 are drawn so as to be slightly apart from one another in a thickness direction for the convenience of illustration. The contour of the absorbent core 22 is drawn by thick broken lines in FIG. 1 for easy understanding of the drawing. As shown in FIG. 1, a width of the absorbent core 22 at each of the front part 201 and the back part 203 is larger than that at the crotch part 202. In other words, the absorbent core 22 is formed in a form of so-called hourglass.

The attachment part 26 shown in FIG. 3 is bonded on an outer surface of the back sheet 23 (i.e., the outer surface is different from a surface facing the absorbent core 22) so as to overlap with the absorbent core 22 (see FIGS. 1 and 2) in a planar view. The attachment part 26 is a loop member of a hook and loop fastener (surface fastener) which is bonded on the back sheet 23 with hot melt adhesive or the like, and the attachment part 26 has a base sheet formed of resin or the like and fine loop structure provided on a surface of the base sheet which is different from the surface bonded on the back sheet 23. The fine loop structure means a group of numerous fine loop elements.

As shown in FIG. 2, the top sheet 21 is bonded on the back sheet 23 at areas around the absorbent core 22 with hot melt adhesive. An outer portion of each side sheet 3 in the left-right direction is bonded on portions of the back sheet 23 which are not covered with the top sheet 21 and bonded on a portion of the top sheet 21 in the vicinity of its side edge in the left-right direction, with hot melt adhesive, and the outer portion lies across the entire length of the side sheet 3 in the longitudinal direction. The side sheet 3 has a side sheet main body 31 and a elastic member 32a extending in the longitudinal direction, and the elastic member 32a is bonded on a free edge of the side sheet main body 31, which is an inner edge part in the left-right direction, with hot melt adhesive.

In both end portions, in the longitudinal direction, of the main body part 2 shown in FIG. 1, an inner portion of each side sheet 3 in the left-right direction (i.e., the inner portion is a portion closer to the central axis of the main body part 2 than the other, with respect to the left-right direction) is bonded on the wearer's side surface of the top sheet 21 with hot melt adhesive. In the crotch part 202 of the main body part 2, two elastic members 32b each extending in the longitudinal direction are bonded at a portion in the vicinity of outer edge of the side sheet 3 in the left-right direction with hot melt adhesive, and the two elastic members 32b are located between the side sheet 3 and the back sheet 23. Polyolefin hot melt adhesive, rubber hot melt adhesive, vinyl acetate hot melt adhesive or the like is used as the above hot melt adhesive. Bonding of the top sheet 21 and the back sheet 23, and bonding of the side sheet 3 and the top sheet 21 may be performed by heat bonding (thermal fusion bonding), ultrasonic bonding or the like.

In each side sheet 3 shown in FIGS. 1 and 2, an inside portion 313 of the side sheet main body 31 which is positioned between both end portions in the longitudinal direction (i.e., the inside portion 313 is a midportion in the longitudinal direction) is not bonded to the top sheet 21 (and the other constituents). By contraction of the elastic member 32a, as shown in FIG. 2, the inside portion 313 stands toward the wearer to become a side wall part (so-called standing gathers) which contacts with the vicinity of wearer's groin. By contraction of the elastic members 32b, the side sheet 3 and the back sheet 23 stand inward and toward the wearer to form leg gathers, and they tightly contact with the vicinity of wearer's groin when the disposable diaper 1 is worn.

As shown in FIG. 1, three elastic members 25 each extending in the left-right direction are provided in each of both end portions of the main body part 2 in the longitudinal direction, and the three elastic members 25 are located between the top sheet 21 and the back sheet 23. In the disposable diaper 1, the elastic members 25 which are bonded to the top sheet 21 and the back sheet 23 in the state where the elastic members 25 are stretched (i.e., the stretched elastic members 25 bonded to the top sheet 21 and the back sheet 23) contract to form waist gathers, and therefore the main body part 2 tightly contacts with the waist of the wearer when the disposable diaper 1 is worn. In the disposable diaper 1, the main body part 2 tightly contacts with the wearer by the elastic members 32a, 32b and elastic members 25, and therefore urine or the like is prevented from leaking out through gaps around the legs and waist of the wearer.

The top sheet 21 is a liquid-pervious sheet material, and the top sheet 21 immediately catches moisture of excrement from the wearer and moves the moisture into the absorbent part 22. For example, the top sheet 21 is a liquid-pervious nonwoven fabric made of hydrophobic fibers (for example, polypropylene, polyethylene, polyester, polyamide or nylon) where hydrophilic treatment is performed on its surface with a surfactant, and for example, a point-bond nonwoven fabric, air-through nonwoven fabric, spunlace nonwoven fabric or spunbond nonwoven fabric is used as the nonwoven fabric. A nonwoven fabric made of hydrophilic fibers such as cellulose, rayon or cotton may be used as the top sheet 21.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, a water-repellent or liquid-impervious plastic film, or a laminated sheet of the nonwoven fabric and the plastic film. The back sheet 23 prevents moisture of excrement or the like which has come to the back sheet 23, from leaking out to the outer side of the main body part 2. In a case where a plastic film is used for the back sheet 23, it is preferable that a plastic film with permeability (breathability) is used, from the view point of preventing sweatiness in the absorbent product 1 and providing comfortable feeling to the wearer.

As the side sheet main body 31, used is a water-repellent or liquid-impervious nonwoven fabric (for example, a spunbond nonwoven fabric, meltblown nonwoven fabric or SMS nonwoven fabric) made of hydrophobic fibers. For example, a polyurethane yarn, strip-like polyurethane film, yarn-like or strip-like natural rubber, or the like is used as the elastic members 32a, 32b, 25. In the present embodiment, a polyurethane yarn is used as each elastic member.

Figure 4:
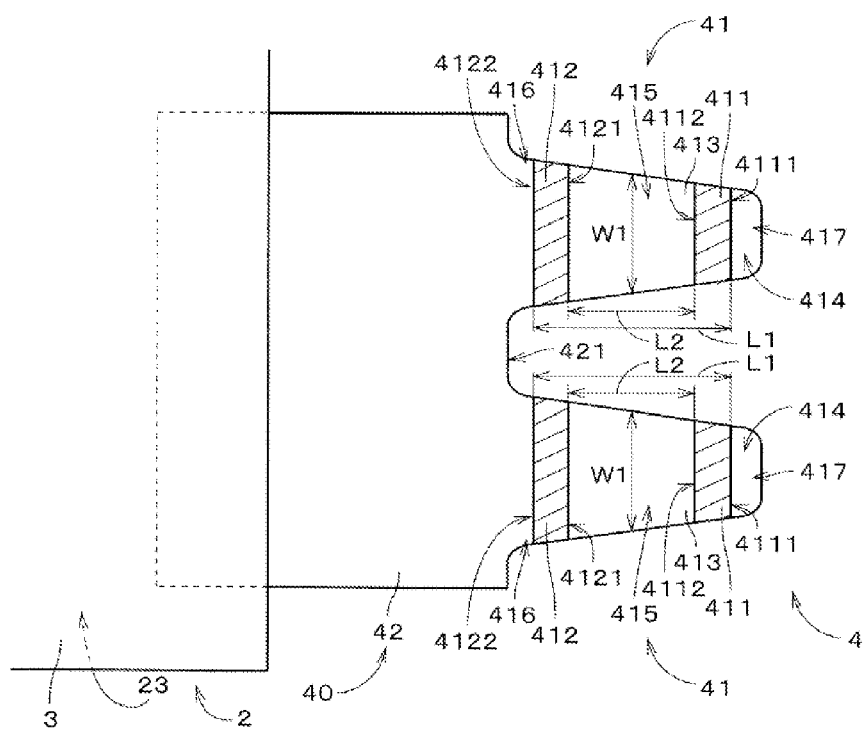
FIG. 4 is an enlarged view showing the vicinity of a connection part.

FIG. 4 is an enlarged view showing the vicinity of one connection part 4 of the pair of connection parts 4. The structure of the other connection part 4 is same as that shown in FIG. 4. Each of the pair of connection parts 4 has two fastening tapes 41 each of which extends in the left-right direction and which are arranged in the longitudinal direction of the main body part 2 (i.e., the longitudinal direction is an up-down direction in FIGS. 1 and 4, and hereinafter it is referred to as a "main body longitudinal direction"), and an approximately rectangular common base 42 which is positioned at the inside of the two fastening tapes 41 in the left-right direction (i.e., the common base 42 is located near the main body part 2). The two fastening tapes 41 have same structure and shape, and a length of each fastening tape 41 in the left-right direction is longer than a length, in the left-right direction, of a portion of the common base 42, the portion not being covered with the main body part 2.

In each connection part 4, each of the two fastening tapes 41 has a band-like (tape-like) tape base 413 extending in the left-right direction, and a first fastening part 411 and a second fastening part 412 provided on one main surface 414 of the tape base 413 (i.e., the one surface 414 is a surface appearing in FIG. 4) so as to lie across the tape base 413 in the main body longitudinal direction. In FIG. 4, hatching lines are drawn at each of the first fastening part 411 and the second fastening part 412 for easy understanding of the drawing. When putting the disposable diaper 1 on the wearer, the main surface 414 of the tape base 413 faces the front part 201 (see FIG. 3) of the main body part 2. Hereinafter it is referred to as an "inner surface 414". In the inner surface 414 of the tape base 413, the second fastening part 412 is located away from the first fastening part 411 toward the main body part 2, and an intermediate area 415 lies between them.

Each of the first fastening part 411 and the second fastening part 412 is a hook member of the hook and loop fastener, the hook member is capable of fastening itself to the attachment part 26 (see FIG. 3) provided on the outer surface of the front part 201 in the main body part 2, and it is bonded on the inner surface 414 of the tape base 413 with hot melt adhesive or the like. Each of the first fastening part 411 and the second fastening part 412 has a base sheet formed of resin or the like and fine hook structure provided on one surface of the base sheet where the other surface of the base sheet is bonded on the tape base 413. The fine hook structure provided on each of the first fastening part 411 and the second fastening part 412 is a group of numerous fine hook elements, and the fine hook structure and the fine loop structure of the attachment part 26 are to engage with each other (i.e., each of the first fastening part 411 and the second fastening part 412 is capable of fastening itself to the attachment part 26).

In each connection part 4, the two tape bases 413 of the two fastening tapes 41 and the common base 42 are portions of one connection sheet 40 formed of resin or the like, and each of the two tape bases 413 projects outward in the left-right direction (toward a direction away from the main body part 2) from the common base 42. An inner end portion of the common base 42 (which is also an inner end portion of the connection sheet 40) is located between the side sheet 3 and the back sheet 23 of the main body part 2 to be bonded thereon, and portions of the common base 42 other than the inner end portion project outward in the left-right direction from the main body part 2.

In other words, the two tape bases 413 are portions of one connection sheet 40 and are continuous with each other through a connection portion of the one connection sheet 40 located near the main body part 2, and the common base 42 which is the connection portion of the two tape bases 413 in the connection sheet 40 protrudes outward from a side edge of the main body part 2 (the common base 42 runs off the side edge). If an outer edge of the top sheet 21 (see FIG. 2) is positioned relatively near an outer edge of the back sheet 23, the inner end portion of the common base 42 may be bonded between the top sheet 21 and the back sheet 23.

In each connection part 4, a width of each of the two fastening tapes 41 (i.e., the width is a length of the tape base 413 in the main body longitudinal direction which is the up-down direction in FIG. 4) gradually decrease toward an outer end in the left-right direction which is a tip of the tape base 413. In each fastening tape 41, each of the first fastening part 411 and the second fastening part 412 is provided on the tape base 413 so as to lie across the entire width of the tape base 413 in the width direction (the width direction is identical to the main body longitudinal direction, and hereinafter referred to as a "tape width direction"). The second fastening part 412 is positioned at the outside of an outer edge 421 of the common base 42 in the left-right direction, and the second fastening part 412 is away from the common base 42.

Hereinafter, a portion of the tape base 413 lying between an inner edge 4122 of the second fastening part 412 which is closer to the main body part 2 than the other edges and an outer edge 421 of the common base 42 is referred to as an "inside area 416". A portion of the tape base 413 lying at the outside of an outer edge 4111 of the first fastening part 411 (i.e., the outer edge 4111 is the edge closer to the tip of the tape base 413 than the other edges) is referred to as an "outside area 417". The above hook member is not provided on the intermediate area 415, the inside area 416 and the outside area 417.

In each fastening tape 41, a distance L1, in the left-right direction, between the outer edge 4111 of the first fastening part 411 and the inner edge 4122 of the second fastening part 412 is larger than a width W1, in the tape width direction, of the tape base 413 at the intermediate area 415 which is the area between the first fastening part 411 and the second fastening part 412 (in the present embodiment, the width of the tape base 413 is the width at the middle of the intermediate area 415 in the left-right direction). Preferably, a length L2, in the left-right direction, of the intermediate area 415 (i.e., the length L2 is a distance, in the left-right direction, between an inner edge 4112 of the first fastening part 411 and an outer edge 4121 of the second fastening part 412) is equal to or larger (greater) than 25% of the width W1 of the tape base 413 at the intermediate area 415, and more preferably the length L2 of the intermediate area 415 is equal to or larger than W1.

As above, since the two fastening tapes 41 have same structure and shape in each connection part 4, L1 in one fastening tape 41 is larger than W1 in the other fastening tape 41, and preferably L2 in one fastening tape 41 is equal to or larger than 25% of W1 in the other fastening tape 41 (more preferably, equal to or larger than W1). In the present embodiment, L2 in the respective fastening tapes 41 are equal to W1. L1 in each fastening tape 41 is about 160% of L2, and a length (width), in the left-right direction, of each of the first fastening part 411 and the second fastening part 412 is about 30% of L2.

In each connection part 4, the connection sheet 40 is formed of white resin material, and the first fastening parts 411 and the second fastening parts 412 are formed of colored resin material other than white. Thus, in each of the two fastening tapes 41, visual recognition of the first fastening part 411 and the second fastening part 412 becomes easy at the side of the inner surface 414 of the tape base 413, and positions of the first fastening part 411 and the second fastening part 412 are visually recognizable (visible) through the tape base 413 at an outer surface side of the tape base 413.

In the disposable diaper 1, since each fastening tape 41 is fastened on the attachment part 26 (see FIG. 3) by the first fastening part 411 and the second fastening part 412 which are away from each other in the left-right direction, the fastening tape 41 can be easily deformed in accordance with motion of the wearer (to follow up the motion). As the result, the fastening tape 41 is prevented from peeling off from the attachment part 26 due to the motion of the wearer or the like.

Figure 5:
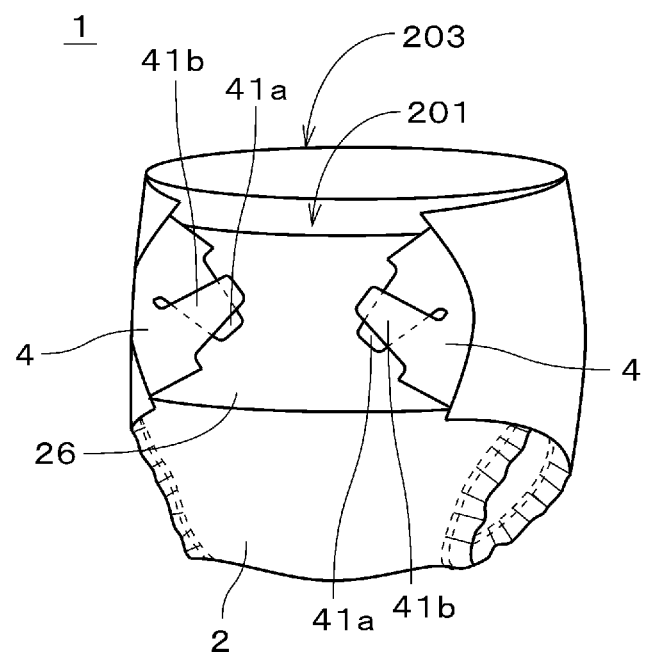
FIG. 5 is a perspective view of the disposable diaper.

In the case where the disposable diaper 1 is large as compared to the wearer's figure or the like (for example, when putting the disposable diaper 1 on a slender (thin) wearer as compared to a normal wearer), out of the two fastening tapes 41 arranged in the main body longitudinal direction in each connection part 4, one fastening tape 41 is fastened on the attachment part 26, and then the other fastening tape 41 is fastened on the attachment part 26 so as to be laid over the one fastening tape 41. In the present embodiment, the fastening tape positioned on the upper side of FIG. 5 (hereinafter, referred to as the "first fastening tape 41a") in each connection part 4 is fastened on the attachment part 26 with its tip obliquely downward, and then the fastening tape positioned on the lower side of FIG. 5 (hereinafter, referred to as the "second fastening tape 41b") is fastened on the attachment part 26 with its tip obliquely upward in the state where the second fastening tape 41b lies on the first fastening tape 41a. Therefore, in the both end portions of the main body part 2 in the longitudinal direction, the front part 201 and the back part 203 fit the waist of the wearer, and both side ends of the main body part fit the vicinity of wearer's groin.

Figure 6:
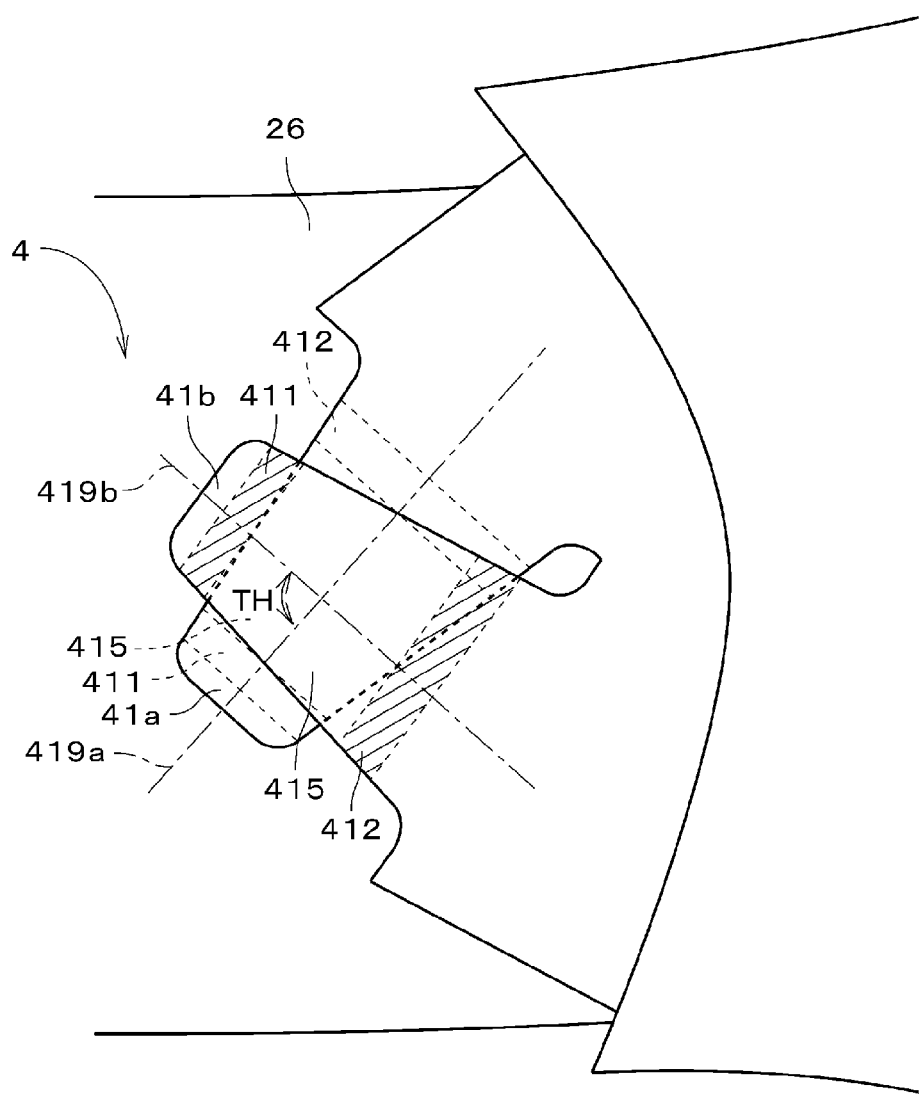
FIG. 6 is an enlarged view showing the vicinity of the connection part.

FIG. 6 is an enlarged view showing the vicinity of one connection part 4 of the pair of connection parts 4. As shown in FIG. 6, the first fastening tape 41a and the second fastening tape 41b overlapping with the first fastening tape 41a intersect almost perpendicularly with each other on the attachment part 26. That is, the first fastening tape 41a and the second fastening tape 41b intersect with each other so that an angle TH formed between a centerline 419a of the first fastening tape 41a and a centerline 419b of the second fastening tape 41b (the centerlines 419a, 419b extend in the left-right direction in the state where the fastening tapes are not fastened) becomes approximate 90 degrees. The intermediate area 415 of the first fastening tape 41a overlaps with the intermediate area 415 of the second fastening tape 41b, and the first fastening part 411 and the second fastening part 412 located at both sides of the intermediate area 415 in the second fastening tape 41b are fastened on the attachment part 26 at both sides of the first fastening tape 41a in the tape width direction (i.e., so as to cross over the first fastening tape 41a). In FIG. 6, hatching lines are drawn at each of the first fastening part 411 and the second fastening part 412 for easy understanding of the drawing.

In order to make the disposable diaper 1 easy to handle when putting the disposable diaper 1 on a wearer or to make the disposable diaper 1 easy to manufacture, a length of each of the first fastening tape 41a and the second fastening tape 41b is limited to a certain value (i.e., the length is made equal to or smaller than the value) in the disposable diaper 1. As the result, an upper limit is set for the distance L1 (see FIG. 4) between the outer edge 4111 of the first fastening part 411 and the inner edge 4122 of the second fastening part 412 in each fastening tape. In the connection part 4, since the intermediate area 415 on which the hook member is not bonded is provided between the first fastening part 411 and the second fastening part 412 in the second fastening tape 41b which is to be laid on (overlapped with) the first fastening tape 41a in fastening the fastening tapes, a total area of fastening parts (i.e., the first fastening part 411 and the second fastening part 412) can be reduced. Therefore, manufacturing cost of the disposable diaper 1 can be reduced.

The distance L1 between the outer edge 4111 of the first fastening part 411 and the inner edge 4122 of the second fastening part 412 in the second fastening tape 41b is made larger than the width W1 (see FIG. 4) of the tape base 413 at the intermediate area 415 in the first fastening tape 41a. Therefore, when the first fastening tape 41a and the second fastening tape 41b are fastened with the second fastening tape 41b lying on the first fastening tape 41a, at least one portion of each of the first fastening part 411 and the second fastening part 412 in the second fastening tape 41b can be easily fastened on the attachment part 26 of the front part 201 without overlapping with the first fastening tape 41a. As the result, the disposable diaper 1 can be made to fit the wearer.

In the disposable diaper 1, since the intermediate area 415 on which the hook member is not bonded is provided between the first fastening part 411 and the second fastening part 412 in the first fastening tape 41a in a similar fashion to the second fastening tape 41b, a total area of the first fastening part 411 and the second fastening part 412 can be reduced. In the case where the second fastening tape 41b is fastened on the attachment part 26 and then the first fastening tape 41a is laid on the second fastening tape 41b to be fastened on the attachment part 26 when putting the disposable diaper 1 on the wearer, at least one portion of each of the first fastening part 411 and the second fastening part 412 in the first fastening tape 41a can be easily fastened on the attachment part 26 without overlapping with the second fastening tape 41b.

In the disposable diaper 1, preferably a distance between an upper end of the outer edge 4111 of the first fastening part 411 and a lower end of the inner edge 4122 of the second fastening part 412 is equal to or larger than the width W1 at the intermediate area 415 in each fastening tape 41. Therefore, at least one portion of each of the first fastening part 411 and the second fastening part 412 in the fastening tape 41, which is to be laid (overlaid) on the other fastening tape 41 in fastening the fastening tapes 41, can be fastened on the attachment part 26 of the front part 201 more easily.

In the connection part 4, the length L2 (see FIG. 4) of the intermediate area 415 of the second fastening tape 41b is made equal to or larger than the width W1 of the intermediate area 415 of the first fastening tape 41a. It is therefore possible to prevent a (portion of) fastening part from being provided on a portion which is more likely not to be used for fastening the second fastening tape 41b (i.e., the portion to be laid on the first fastening tape 41a), when the second fastening tape 41b is laid on the first fastening tape 41a to be fastened on the attachment part 26, and a total area of the fastening parts can be further reduced. In addition, the length L2 of the intermediate area 415 of the first fastening tape 41a is made equal to or larger than the width W1 of the intermediate area 415 of the second fastening tape 41b. It is therefore possible to prevent a (portion of) fastening part from being provided on a portion which is more likely not to be used (i.e., the portion has a small chance of being used) for fastening the first fastening tape 41a (i.e., the portion to be laid on the second fastening tape 41b), when the first fastening tape 41a is laid on the second fastening tape 41b to be fastened on the attachment part 26, and a total area of the fastening parts can be further reduced.

In the disposable diaper 1, the distance between an upper end of the inner edge 4112 of the first fastening part 411 and a lower end of the outer edge 4121 of the second fastening part 412 is preferably equal to or greater than the width W1 of the intermediate area 415 in each fastening tape 41. It is therefore possible to prevent a (portion of) fastening part from being provided on a portion which is more likely not to be used for fastening one fastening tape 41 to be laid on the other fastening tape in fastening the fastening tapes 41 (i.e., when the fastening tapes 41 are fastened in an overlapping manner), and a total area of the fastening parts can be further reduced.

When the fastening tapes are fastened in an overlapping manner in the connection part 4, the angle TH formed between the centerline 419a of the first fastening tape 41a and the centerline 419b of the second fastening tape 41b is not necessarily limited to approximate 90 degrees, and the first fastening tape 41a and the second fastening tape 41b may be overlapped with each other so that the angle TH (i.e., the angle formed between portions of the centerline 419a and the centerline 419b which are from an intersection of the centerline 419a and the centerline 419b to tips of the first fastening tape 41a and the second fastening tape 41b, respectively) becomes, for example, equal to or more than 30 degrees and equal to or less than 90 degrees.

In the connection part 4, if the length L2 of the intermediate area 415 of the second fastening tape 41b is made equal to or larger than 25% of the width W1 of the intermediate area 415 of the first fastening tape 41a, it is possible to prevent, to some extent, a (portion of) fastening part from being provided on a portion which is more likely not to be used for fastening the second fastening tape 41b when the second fastening tape 41b is laid on the first fastening tape 41a to be fastened on the attachment part 26 under the condition where the angle TH is within a range in normal fastening operation. Also a total area of the fastening parts can be reduced.

In the case where the length L2 of the intermediate area 415 of the first fastening tape 41a is made equal to or larger than 25% of the width W1 of the intermediate area 415 of the second fastening tape 41b, it is possible to further prevent a (portion of) fastening part from being provided on a portion which is more likely not to be used for fastening the first fastening tape 41a when the first fastening tape 41a is laid on the second fastening tape 41b to be fastened on the attachment part 26 under the condition where the angle TH is within a range in normal fastening operation. As the result, a total area of the fastening parts can be further reduced.

In the connection part 4, the width of each of the first fastening tape 41a and the second fastening tape 41b gradually decreases toward the tip of the tape base 413 (i.e., the width of a position becomes narrower as the position comes closer to the tip of the tape base 413). Thus, when the fastening tapes are fastened, the first fastening part 411 of one fastening tape which is fastened later than the other fastening tape (i.e., the one fastening tape is laid on the other fastening tape to be fastened on the attachment part 26) can be easily fastened on the attachment part 26 with avoiding the other fastening tape (which is fastened earlier than the one fastening tape). As the result, the tip portion of the one fastening tape to be fastened on the attachment part 26 later can be fastened on the attachment part 26 securely.

In the connection part 4, the two tape bases 413 of the first fastening tape 41a and the second fastening tape 41b are portions of one connection sheet 40 and are continuous with each other through the common base 42 of the connection sheet 40 located near the main body part 2, and the second fastening parts 412 of the first fastening tape 41a and the second fastening tape 41b lie at an outside, with respect to the left-right direction, of the common base 42 of the connection sheet 40. Thus, it is possible to prevent stiffness of root portions of the first fastening tape 41a and the second fastening tape 41b (i.e., the root portions are between the second fastening parts 412 and the common base 42) from being excessively large (overlarge) and to easily deform the first fastening tape 41a and the second fastening tape 41b at the root portions. As the result, the first fastening tape 41a and the second fastening tape 41b can be easily fastened in an overlapping manner. In addition, since the common base 42 protrudes outward (laterally) from the side edge of the main body part 2, the first fastening tape 41a and the second fastening tape 41b can be easily made to be close to each other by deforming the common base 42. As the result, fastening of the first fastening tape 41a and the second fastening tape 41b in an overlapping manner can be performed more easily.

Furthermore, positions of the first fastening part 411 and the second fastening part 412 are recognizable at the outer surface side of the tape base 413 in each of the first fastening tape 41a and the second fastening tape 41b. Therefore, when the first fastening tape 41a and the second fastening tape 41b are fastened in an overlapping manner, an overlapping area of the intermediate areas 415 of the two fastening tapes can be easily increased. In other words, the first fastening part 411 and the second fastening part 412 of the fastening tape which is fastened on the attachment part 26 later than the other fastening tape can be prevented from overlapping extensively with the other fastening tape. As the result, the fastening tape fastened on the attachment part 26 later can be fastened on the attachment part 26 securely.

In the above disposable diaper 1, a fastening strength, per unit area, of the first fastening part 411 to the attachment part 26 is equal to a fastening strength, per unit area, of the second fastening part 412 to the attachment part 26 in each fastening tape, and the width of the first fastening part 411 in the left-right direction is equal to the width of the second fastening part 412 in the left-right direction. Thus, the first fastening part 411 and the second fastening part 412 can be formed with one long hook member, and manufacture of the connection part 4 can be simplified.

In another example of disposable diaper in accordance with the present invention, the fastening strength of the first fastening part 411 to the attachment part 26 is larger (higher) than the fastening strength of the second fastening part 412 to the attachment part 26. In the disposable diaper, when force in a direction to peel off the fastening tape is applied in the case where the tape base 413 of the fastening tape is adhered to clothes of the wearer or the like, the first fastening part 411 which is closer to the tip of the tape base 413 is often applied with greater force than the second fastening part 412. Thus, the fastening strength of the first fastening part 411 to the attachment part 26 is made larger than that of the second fastening part 412 as described above, and therefore unintentional peel-off of the fastening tape can be suppressed.

The difference between the fastening strength of the first fastening part 411 to the attachment part 26 and the fastening strength of the second fastening part 412 to the attachment part 26, may be achieved by, for example, making an area of the first fastening part 411 larger than an area of the second fastening part 412, or by utilizing a hook member as the first fastening part 411, the hook member having stronger fastening strength per unit area to the attachment part 26 than that of the second fastening part 412.

Though the preferred embodiments of the present invention have been discussed above, the present invention is not limited to the above-discussed preferred embodiments, but allows various variations.

For example, there may be a case where each of the first fastening part 411 and the second fastening part 412 in each fastening tape 41 is a loop member of a hook and loop fastener and the attachment part 26 provided on the front part 201 of the main body part 2 is a hook member of the hook and loop fastener. In each fastening tape 41, fine hook structure or fine loop structure may be directly formed on the inner surface 414 of the tape base 413 to be the first fastening part 411 or the second fastening part 412. In the main body part 2, fine hook structure or fine loop structure may be directly formed on the outer surface of the front part 201 to be the attachment part 26. In other words, one of fine hook structure and fine loop structure which engage with each other is formed on the front part 201 of the main body part 2, and the other is formed on each of the first fastening part 411 and the second fastening part 412 of each fastening tape 41 in the disposable diaper 1. Therefore, the fastening tapes 41 can be fastened on the attachment part 26 securely. In addition, fine hook structure is formed on the first fastening part 411 and the second fastening part 412, fine loop structure is formed on the attachment part 26, and therefore, when manufacturing and wearing the disposable diaper 1, the attachment part 26 having relatively large area can be prevented from adhering to another portion of the disposable diaper 1 or the like, to make manufacturing and wearing the disposable diaper 1 easy.

In the disposable diaper 1, fine hook structure or fine loop structure is not necessarily formed on the first fastening part 411 and the second fastening part 412 of each fastening tape 41. For example, there may be a case where the first fastening part 411 and the second fastening part 412 are adhesive layers which are formed of adhesive material on the tape base 413 made of nonwoven fabric, and the attachment part 26 is a plastic film on which the adhesive layers can adhere.

In each fastening tape 41, positions of the first fastening part 411 and the second fastening part 412 may be made recognizable at the outer surface side of the tape base 413 by, for example, printing marks, which indicate the positions of the first fastening part 411 and the second fastening part 412, on the outer surface of the tape base 413.

The common base 42 is not necessarily provided in each connection part 4, and the end of the tape base 413 in each of the two fastening tapes 41 may be bonded to the main body part 2 directly. The width of each fastening tape 41 may be, for example, constant across almost the entire length of the tape base 413 in the left-right direction.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 disposable diaper
2 main body part
4 connection part
26 attachment part
40 connection sheet
41 fastening tape
41*a* first fastening tape
41*b* second fastening tape
201 front part
202 crotch part
203 back part
411 first fastening part
412 second fastening part
413 tape base
414 inner surface
4111 outer edge
4122 inner edge
L1 distance
L2 length
W1 width

The invention claimed is:

1. A disposable diaper, comprising:
    a sheet-like main body part having a front part, a crotch part and a back part which are arranged in this order along a longitudinal direction; and
    a pair of connection parts attached to both side portions of said back part, said pair of connection parts being to be fastened to an outer surface of said front part to connect said both side portions with both side portions of said front part; wherein
    each of said pair of connection parts comprises two fastening tapes each extending in a left-right direction, said two fastening tapes being arranged in a longitudinal direction, and
    each of said two fastening tapes comprises:
    a band-like tape base;
    a first fastening part provided on an inner surface of said tape base so as to lie across said tape base in said longitudinal direction and comprising a first outer edge distal to said main body part and a first inner edge proximal to said main body part, said first fastening part being capable of fastening itself to said outer surface of said front part; and
    a second fastening part provided on said inner surface of said tape base so as to lie across said tape base in said longitudinal direction and comprising a second outer edge distal to said main body part and a second inner edge proximal to said main body part, said second fastening part being away from said first fastening part toward said main body part and being capable of fastening itself to said outer surface of said front part; and
    an intermediate area between said first inner edge and said second outer edge, wherein
    a distance between the first outer edge and the second inner edge in one fastening tape, is larger than a width of said intermediate area in the other fastening tape.

2. The disposable diaper according to claim 1, wherein a length, in said left-right direction, of an area between said first fastening part and said second fastening part in said one fastening tape is equal to or larger than 25% of said width of said intermediate area in said other fastening tape.

3. The disposable diaper according to claim 2, wherein positions of said first fastening part and said second fastening part are recognizable at an outer surface side of said tape base in each of said two fastening tapes.

4. The disposable diaper according to claim 2, wherein said length, in said left-right direction, of said area between said first fastening part and said second fastening part in said one fastening tape is equal to or larger than said width of said intermediate area in said other fastening tape.

5. The disposable diaper according to claim 4, wherein positions of said first fastening part and said second fastening part are recognizable at an outer surface side of said tape base in each of said two fastening tapes.

6. The disposable diaper according to claim 1, wherein a width of each fastening tape gradually decreases toward a tip of said tape base.

7. The disposable diaper according to claim 6, wherein positions of said first fastening part and said second fastening part are recognizable at an outer surface side of said tape base in each of said two fastening tapes.

8. The disposable diaper according to claim 1, wherein a fastening strength of said first fastening part to said front part is larger than that of said second fastening part.

9. The disposable diaper according to claim 8, wherein positions of said first fastening part and said second fastening part are recognizable at an outer surface side of said tape base in each of said two fastening tapes.

10. The disposable diaper according to claim 1, wherein
    two tape bases of said two fastening tapes are portions of one sheet in each of said pair of connection parts, and said two tape bases are continuous with each other through a connection portion of said one sheet located near said main body part, and
    second fastening parts of said two fastening tapes lie at an outside, with respect to said left-right direction, of said connection portion in said one sheet.

11. The disposable diaper according to claim 10, wherein positions of said first fastening part and said second fastening part are recognizable at an outer surface side of said tape base in each of said two fastening tapes.

12. The disposable diaper according to claim 1, wherein
    two tape bases of said two fastening tapes are portions of one sheet in each of said pair of connection parts, and said two tape bases are continuous with each other through a connection portion of said one sheet located near said main body part, and
    said connection portion in said one sheet protrudes outward from a side edge of said main body part.

13. The disposable diaper according to claim 12, wherein positions of said first fastening part and said second fastening part are recognizable at an outer surface side of said tape base in each of said two fastening tapes.

14. The disposable diaper according to claim 1, wherein one of fine hook structure and fine loop structure which engage with each other is provided on said front part of said main body part, and the other is provided on each of said first fastening part and said second fastening part.

15. The disposable diaper according to claim 14, wherein positions of said first fastening part and said second fastening part are recognizable at an outer surface side of said tape base in each of said two fastening tapes.

16. The disposable diaper according to claim 1, wherein positions of said first fastening part and said second fastening part are recognizable at an outer surface side of said tape base in each of said two fastening tapes.

* * * * *